United States Patent
Klingler et al.

(10) Patent No.: US 7,511,147 B2
(45) Date of Patent: Mar. 31, 2009

(54) PROCESS FOR MANUFACTURING OF CHIRAL LOBELIN

(75) Inventors: Franz-Dietrich Klingler, Griesheim (DE); Rainer Sobotta, Ingelheim (DE)

(73) Assignee: Boehringer Ingelheim Pharma GmbH & Co. KG, Infelheim (DE)

( * ) Notice: Subject to any disclaimer, the term of this patent is extended or adjusted under 35 U.S.C. 154(b) by 608 days.

(21) Appl. No.: 11/178,193

(22) Filed: Jul. 8, 2005

(65) Prior Publication Data

US 2006/0014791 A1    Jan. 19, 2006

(30) Foreign Application Priority Data

Jul. 17, 2004    (DE) .................. 10 2004 034 682

(51) Int. Cl.
*C07D 211/20* (2006.01)

(52) U.S. Cl. .................................. 546/237

(58) Field of Classification Search .............. 546/237
See application file for complete search history.

(56) References Cited

U.S. PATENT DOCUMENTS 1,946,345 A * 2/1934 Wieland .................. 546/237

OTHER PUBLICATIONS

Kriz et al. "Preparation of lobeline . . ." CA 114:247574 (1991).*
Bellus et al. "Lobelia alkaloids . . ." CA 61:11490 (1964).*
Takeda et al. "Practical asymmetric synthesis . . ." Tetrahedron Lett. 30(3) p. 367-370 (1989).*
Ojima et al. "Synthesis of chiral dipeptides . . ." CA 96:123292 (1982).*
Sakuraba et al. "An efficient synthesis of . . ." Tetrahedron Assymmetry v.4, issue 7, abstract (1993).*

* cited by examiner

*Primary Examiner*—Celia Chang
(74) *Attorney, Agent, or Firm*—Michael P. Morris; Mary-Ellen M. Devlin; Alan R. Stempel

(57) ABSTRACT

The present invention relates to a shortened process for preparing L-lobeline by rhodium-catalysed asymmetric hydrogenation on an industrial scale.

11 Claims, No Drawings

PROCESS FOR MANUFACTURING OF CHIRAL LOBELIN

The present invention relates to a shortened process for manufacturing L-lobeline by rhodium-catalysed asymmetric hydrogenation on an industrial scale.

TECHNOLOGICAL BACKGROUND TO THE INVENTION

Lobeline is one of the lobelia alkaloids of *Lobelia inflata* (Indian tobacco, Emetic Weed, Asthma Weed) and is native to the eastern and central states of the USA and Canada. The plant contains about 0.3% alkaloids. The lobelia alkaloids are 2,6-disubstituted piperidine derivatives. Of the 20 or so lobelia alkaloids, lobeline is the main alkaloid. Lobeline is a respiratory stimulant when administered parenterally (3-10 mg) and was previously used as a respiratory analeptic to treat asthma, collapse and anaesthetic accidents. When taken orally it is rapidly broken down and therefore ineffective. As lobeline intensifies the effects of nicotine and thus induces retching and nausea, it has been developed clinically as a sustained-release agent for breaking the smoking habit (Drug News (25.3) 1996, 6).

PRIOR ART

The synthesis of L-lobeline is known in the art. Methods used hitherto, however, involve a relatively high number of reaction steps. Thus, for example, a fairly recent publication on this subject proposes a stereoselective synthesis of lobeline which starts from benzaldehyde and takes 17 reaction steps before the product is obtained (Felpin et al., J. Org. Chem (2002) 67, 9192).

The aim of the present invention is therefore to provide a shorter process for preparing L-lobeline.

Surprisingly, it has now been found that lobeline of formula I can be obtained in good yields and good optical purity on an industrial scale if a corresponding diketone II is subjected to asymmetric hydrogenation in the presence of rhodium and a chiral bidentate phosphine ligand as catalyst system.

DETAILED DESCRIPTION OF THE INVENTION

The present invention relates to a process for preparing L-lobeline of formula I,

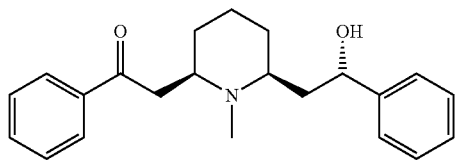

I or an acid addition salt thereof, starting from lobelanine of formula II,

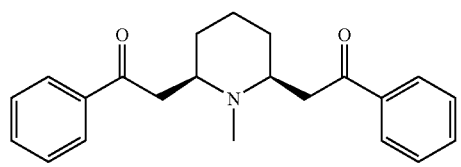

II or an acid addition salt thereof, characterised in that the latter is subjected to asymmetric hydrogenation in the presence of a catalyst system consisting of rhodium and (2R,4R)-4-(dicyclohexylphosphino)-2-(diphenylphosphino-methyl)-N-methyl-aminocarbonyl-pyrrolidine, optionally an inert diluent and a weak base.

The starting product of formula II can be obtained by simply reacting 3-oxo-3-phenylpropionic acid, 1,5-pentanedione and methylamine-hydrochloride in acetone in the presence of a citrate buffer. 3-Oxo-3-phenylpropionic acid can be obtained by saponifying the corresponding ethyl ester.

The inert diluent used may be either protic solvents such as alcohols and/or water or aprotic polar solvents such as e.g. ethers and/or amides or lactams and/or mixtures thereof. Water may optionally be added to all the solvents. Preferably, branched or unbranched $C_{1-8}$ alcohols are used as the protic solvents. Lower alcohols such as methanol, ethanol, n-propanol and iso-propanol or mixtures thereof are particularly preferred. The reaction medium used is most preferably methanol, while this methanol or the other alcohols or solvents may optionally contain water. Suitable aprotic solvents are polar ethers such as tetrahydrofuran or dimethoxyethyl-ether or amides such as, for example, dimethylformamide, or lactams such as N-methylpyrrolidone. Preferably, solvents with low flammability are used.

Preferably in the above process the hydrogenation is carried out in the presence of less than one equivalent of a weak base selected from among the tertiary amines, alkali metal hydrogen carbonates and alkali metal carbonates.

Suitable organic bases are tertiary amines, especially tertiary alkyl amines, tertiary alkyl arylamines or pyridines. Preferably, trialkylamines with branched or unbranched $C_{1-6}$ alkyl groups are used. It has proved particularly preferable to use triethylamine or diisopropylethylamine, for example. If desired, the reaction may also be carried out in the presence of basic polymers with, for example, tertiary amino functions.

Preferably in the above process the asymmetric hydrogenation is carried out in a temperature range of from 0° C. to 100° C., preferably 20-80° C., particularly preferably 40-60° C.

Also preferably, in the above process, the asymmetric hydrogenation is carried out under a pressure of 1 to 40 bar, preferably 10 to 30 bar, most preferably 15 to 25 bar.

In a preferred embodiment of the invention the process is carried out under a protective gas atmosphere, preferably a nitrogen or argon atmosphere, or mixtures thereof.

Most preferably, in the above process, a compound of formula II or an acid addition salt thereof is used in a molar ratio to the rhodium catalyst of 500:1 to 100000:1, most preferably 750:1 to 20000:1, during asymmetric hydrogenation.

Consequently, the invention most preferably relates to a process for preparing L-lobeline in which the following steps are carried out:

dissolving lobelanine in methanol, adding triethylamine in methanol, adding the catalyst solution, preferably in a molar ratio of 500:1 to 100000:1, more preferably 750:1 to 20000:1, subjecting the reaction mixture to hydrogen, heating the reaction mixture to 20-80° C., preferably 40-60° C., more preferably 47-53° C. and adjusting the hydrogen pressure to 10-30 bar, preferably 15-25 bar, more preferably 20, after the end of the reaction, distilling off the methanol under reduced pressure.

The reaction may be worked up in the usual way, e.g. by optionally deactivating and removing the catalyst, eliminating the solvent and isolating the pure end product from the residue by crystallisation, distillation, extraction or chromatography.

The invention preferably relates to a process in which the following steps are carried out in order to isolate the product:
(i) distributing the reaction mixture obtained during asymmetric hydrogenation between water and an organic solvent,
(ii) adjusting the aqueous phase to a pH in the acidic range,
(iii) separating off the aqueous phase,
(iv) optionally repeating steps (i) to (iii)
(v) adjusting the aqueous phase to a pH in the basic range;
(vi) distributing the reaction mixture between water and an organic solvent,
(vii) optionally repeating steps (v) to (vi)
(viii) separating off the organic phase formed and concentrating it,
(ix) crystallising the product.

Particularly preferably, in the above process followed by isolation according to steps (i) to (ix), the organic solvent is toluene.

Most preferably, in the above process followed by isolation according to steps (i) to (ix), the product in step (ix) is crystallised by the addition of a $C_{1-8}$-alcohol, preferably iso-propanol.

Terms and Definitions Used

By the term $C_{1-8}$-alcohol are meant branched and unbranched alcohols having 1 to 8 carbon atoms and one or two hydroxy groups. Accordingly, by the term $C_{1-4}$ alcohols are meant branched and unbranched alkyl groups having 1 to 4 carbon atoms and one or two hydroxy groups. Alcohols with 1 to 4 carbon atoms are preferred. Examples of these include: methanol, ethanol, n-propanol, iso-propanol, n-butanol, iso-butanol, sec-butanol, tert-butanol, n-pentanol, iso-pentanol, neo-pentanol or hexanol. In some cases the abbreviations MeOH, EtOH, n-PrOH, i-PrOH, n-BuOH, i-BuOH, t-BuOH, etc, are used for the above mentioned molecules. Unless otherwise stated, the definitions propanol, butanol, pentanol and hexanol include all the possible isomeric forms of the groups in question. Thus, for example, propanol also includes n-propanol and iso-propanol while butanol includes iso-butanol, sec-butanol and tert-butanol, etc.

The compounds of formula I and II may optionally be converted into the acid addition salts thereof with an inorganic or organic acid. Suitable acids include for example succinic acid, hydrobromic acid, acetic acid, fumaric acid, maleic acid, methanesulphonic acid, lactic acid, oxalic acid, phosphoric acid, hydrochloric acid, sulphuric acid, tartaric acid or citric acid. It is also possible to use mixtures of the above mentioned acids.

The process according to the invention will now be illustrated by means of the examples that follow. The skilled man will be aware that the examples serve only as an illustration and are not to be regarded as restrictive.

EXAMPLES

Preparation of the Catalyst Solution

A 3 l glass apparatus is flushed with argon and filled with 2 l of methanol. The methanol is refluxed for 1 hours while argon is piped through. After cooling to 20-25° C., 7.2 g of di-chloro-bis-[(cycloocta-1,5-diene)rhodium (I) and 9.8 g of (2R,4R)-4-(dicyclohexyl-phosphino)-2-(diphenylphosphinomethyl)-N-methylaminocarbonyl-pyrrolidine are added in an argon countercurrent. The contents are stirred for 30 minutes at 20-25° C. During this time the two catalyst components dissolve, apart from a small residual amount.

Hydrogenation 90 kg of lobelanine hydrochloride are placed in a 300 l stirred apparatus and then 174 kg of methanol are added. The contents are then stirred for 5 minutes and the suspension is added to an inertised 500 l autoclave. A solution of 0.65 l of triethylamine in 35.6 kg of methanol is added to the autoclave through the 300 l stirred apparatus. The stirrer of the autoclave is started up and set to 400-500 rpm. The autoclave is evacuated down to 700 mbar and then nitrogen gas is introduced up to 1.5 bar. This process is repeated 10 times and the apparatus is then set to normal pressure.

The catalyst solution is metered into the autoclave and then subjected to a hydrogen pressure of 4 bar. The excess pressure is released into the vacuum pump. This procedure is repeated 4 times. The autoclave contents are heated to 47-53° C., the hydrogen pressure is adjusted to 20 bar and the stirrer set to its maximum speed. Hydrogenation is ended when the hydrogen uptake is 120% of theory (130.1 bar). The autoclave contents are cooled to 20-25° C. The autoclave is then evacuated (700 mbar) and equalised with nitrogen. The hydrogenating solution is transferred into a 500 l stirred apparatus and the methanol is distilled off under reduced pressure at 50-60° C. (at 45-50° C. towards the end of distillation). 100 l of water, 50 l of toluene and 1.2 l of 32% hydrochloric acid are added to the residue. The stirrer is started up and the mixture is stirred vigorously for about 20 minutes (at 35-40° C., pH: 0.5-1.5). After the stirrer has been switched off the phases are left to settle and the aqueous phase is removed. Then the aqueous phase is extracted again with 30 l of toluene. The aqueous phase is placed in a 500 l stirred apparatus and 150 l of toluene and 23.1 kg of 45% sodium hydroxide solution are added. The stirrer is started up and the mixture is stirred vigorously for about 20 minutes (at 35-40° C., pH: 12-13). After the aqueous phase has been removed the mixture is extracted twice more with 40 l and 25 l of toluene. The toluene phases are combined in a 500 l stirred apparatus, 50 l of water are added and the whole is mixed thoroughly. When the stirrer has been switched off the phases are left to settle and the lower aqueous phase is removed. Then the toluene phase is extracted again with 50 l of water. After the aqueous phase has been removed again the toluene phase is evaporated down at 50-60° C. under 65-80 mbar. Distillation ends at 40° C. at 4 to 10 mbar. 30 l of iso-propanol are added to the residue and this is distilled off again with residual toluene at 40-45° C. in vacuo. After a further 120 l of iso-propanol have been added the mixture is cooled to 17-23° C. with slow stirring and the contents of the apparatus are stirred at this temperature for 3 days. The mixture is then cooled to −5 to −10° C. and stirred for a further 2 hours. The crystal suspension is then centrifuged. The crystallised material is washed with 50 l of toluene and dried at 40-50° C. in the vacuum drying cupboard. Yield: l-lobeline, 22.2-28.6 kg; 29-35% of theory.

What is claimed is:

1. A process for preparing L-lobeline of formula I,

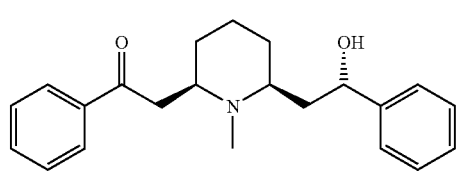

I or an acid addition salt thereof, starting from lobelanine of formula II,

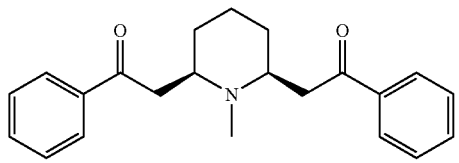

or an acid addition salt thereof, wherein the latter is subjected to asymmetric hydrogenation in the presence of a catalyst system consisting of rhodium and (2R,4R)-4-(dicyclohexylphosphino)-2-(diphenylphosphino-methyl)-N-methyl-aminocarbonyl-pyrrolidine, optionally an inert diluent and a weak base.

2. The process according to claim 1, wherein the hydrogenation is carried out in the presence of less than one equivalent of a weak base selected from the group consisting of tertiary amines.

3. The process according to claim 1, wherein the asymmetric hydrogenation is carried out in a temperature range from 0° C. to 100° C.

4. The process according to claim 1, wherein the asymmetric hydrogenation is carried out at a pressure of 1 to 40 bar.

5. The process according to claim 1, wherein the asymmetric hydrogenation is carried out in a protic diluent.

6. The process according to claim 5, wherein the hydrogenation is carried out under protective gas.

7. The process according to claim 1, wherein a compound of formula II or an acid addition salt thereof is used in the asymmetric hydrogenation in a molar ratio of 500:1 to 100000:1 in relation to the rhodium catalyst.

8. The process according to claim 7, wherein the following steps are carried out:
a) dissolving lobelanine in methanol,
b) adding triethylamine in methanol,
c) adding the catalyst solution,
d) treating the reaction mixture with hydrogen,
e) heating the reaction mixture to 20-80° C. and adjusting the hydrogen pressure to 10-30 bar, and
f) after the end of the reaction, distilling off the methanol under reduced pressure.

9. The process according to one of claim 1, wherein the following steps are carried out in order to isolate the product:
(i) distributing the reaction mixture obtained during asymmetric hydrogenation between water and an organic solvent,
(ii) adjusting the aqueous phase to a pH in the acidic range,
(iii) separating off the aqueous phase,
(iv) optionally repeating steps (i) to (iii)
(v) adjusting the aqueous phase to a pH in the basic range;
(vi) distributing the reaction mixture between water and an organic solvent,
(vii) optionally repeating steps (v) to (vi)
(viii) separating off the organic phase formed and concentrating it,
(ix) crystallising the product.

10. The process according to claim 9, wherein the organic solvent is toluene.

11. The process according to claim 9, wherein the product in step (ix) is crystallised by the addition of a $C_{1-8}$-alcohol.

* * * * *